United States Patent [19]
Okazaki

[11] Patent Number: 5,005,580
[45] Date of Patent: Apr. 9, 1991

[54] DESTROYING WAVE TREATMENT APPARATUS

[75] Inventor: Kiyoshi Okazaki, Takanezawa, Japan

[73] Assignee: Kabushiki Kaisha Toshiba, Kawasaki, Japan

[21] Appl. No.: 445,154

[22] Filed: Dec. 6, 1989

Related U.S. Application Data

[63] Continuation of Ser. No. 340,352, Apr. 19, 1989, abandoned.

[30] Foreign Application Priority Data

Apr. 22, 1988 [JP] Japan .................................. 63-98312
Feb. 22, 1989 [JP] Japan .................................. 1-44845

[51] Int. Cl.⁵ ............................................... A61B 8/00
[52] U.S. Cl. ............................. 128/660.03; 128/24 A
[58] Field of Search ................. 128/24 A, 328, 660.03

[56] References Cited

U.S. PATENT DOCUMENTS

| | | | |
|---|---|---|---|
| 4,425,580 | 1/1984 | Haendle et al. | 128/653 X |
| 4,787,371 | 11/1988 | Grasser et al. | 128/328 S X |
| 4,796,613 | 1/1989 | Heumann et al. | 128/24 A |
| 4,803,995 | 2/1989 | Ishida et al. | 128/328 S X |
| 4,819,621 | 4/1989 | Ueberle et al. | 128/24 A |
| 4,821,730 | 4/1989 | Wurster et al. | 128/328 X |

FOREIGN PATENT DOCUMENTS

| | | |
|---|---|---|
| 0242511A1 | 2/1987 | European Pat. Off. . |
| 0257199A1 | 5/1987 | European Pat. Off. . |
| 3124584A1 | 1/1983 | Fed. Rep. of Germany . |
| 3713816A1 | 1/1987 | Fed. Rep. of Germany . |
| 3743883A1 | 7/1988 | Fed. Rep. of Germany . |
| 3826709A1 | 2/1989 | Fed. Rep. of Germany . |

OTHER PUBLICATIONS

German Search Report for German Pat. Appln. P 39 13 023.1-35, dated Jun. 1, 1990 (with English translation).
Okazaki, commonly assigned, U.S. patent application Ser. No. 07/293,284, filed Jan. 4, 1989.

*Primary Examiner*—Francis Jaworski
*Attorney, Agent, or Firm*—Finnegan, Henderson, Farabow, Garrett, and Dunner

[57] ABSTRACT

A destroying wave treatment apparatus collects tomogram data before and during the transmission of a destroying wave by a destroying wave applicator. An image processing circuit processes the tomogram data to form a subtraction image. A display displays tomograms before and during the transmission of the destroying wave. Therefore, an operator may start and stop the transmission of the destroying wave while seeing those images.

5 Claims, 6 Drawing Sheets

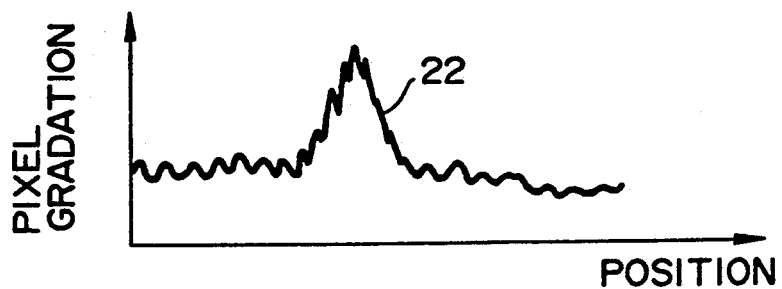
F I G. 4A
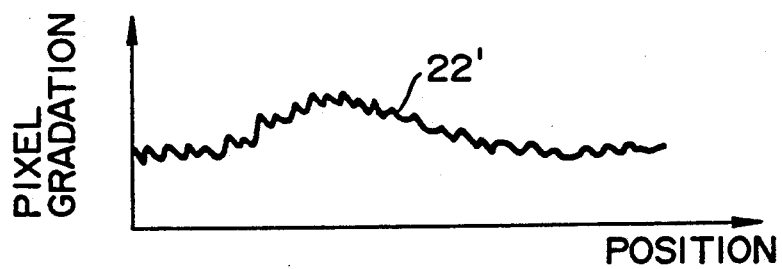
F I G. 4B
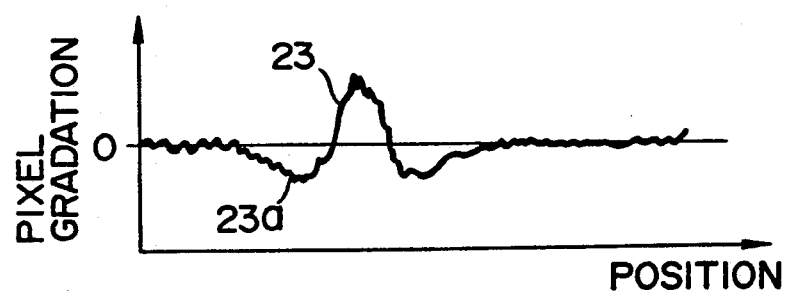
F I G. 4C

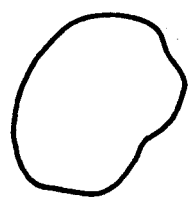
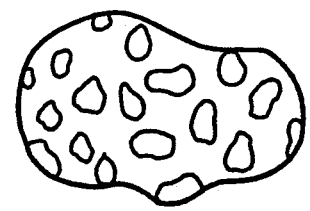
FIG. 5A      FIG. 5B
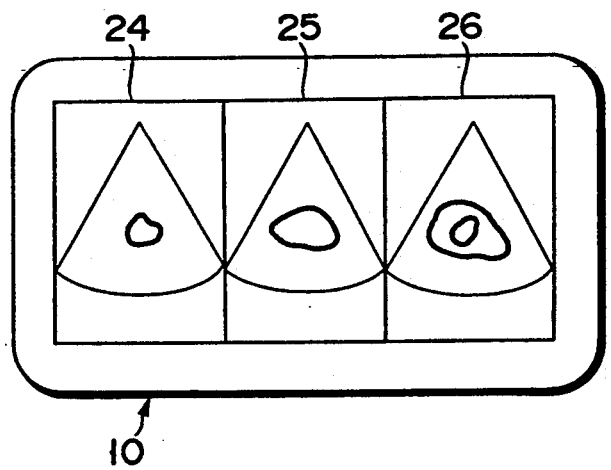
FIG. 6
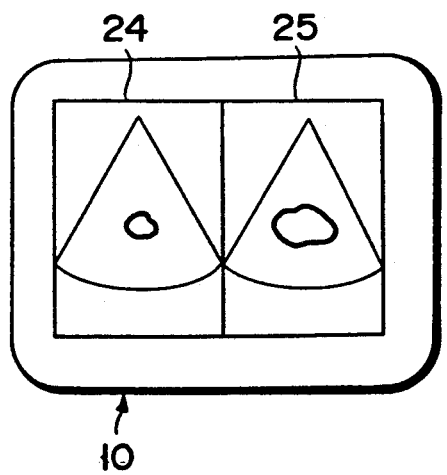
FIG. 8

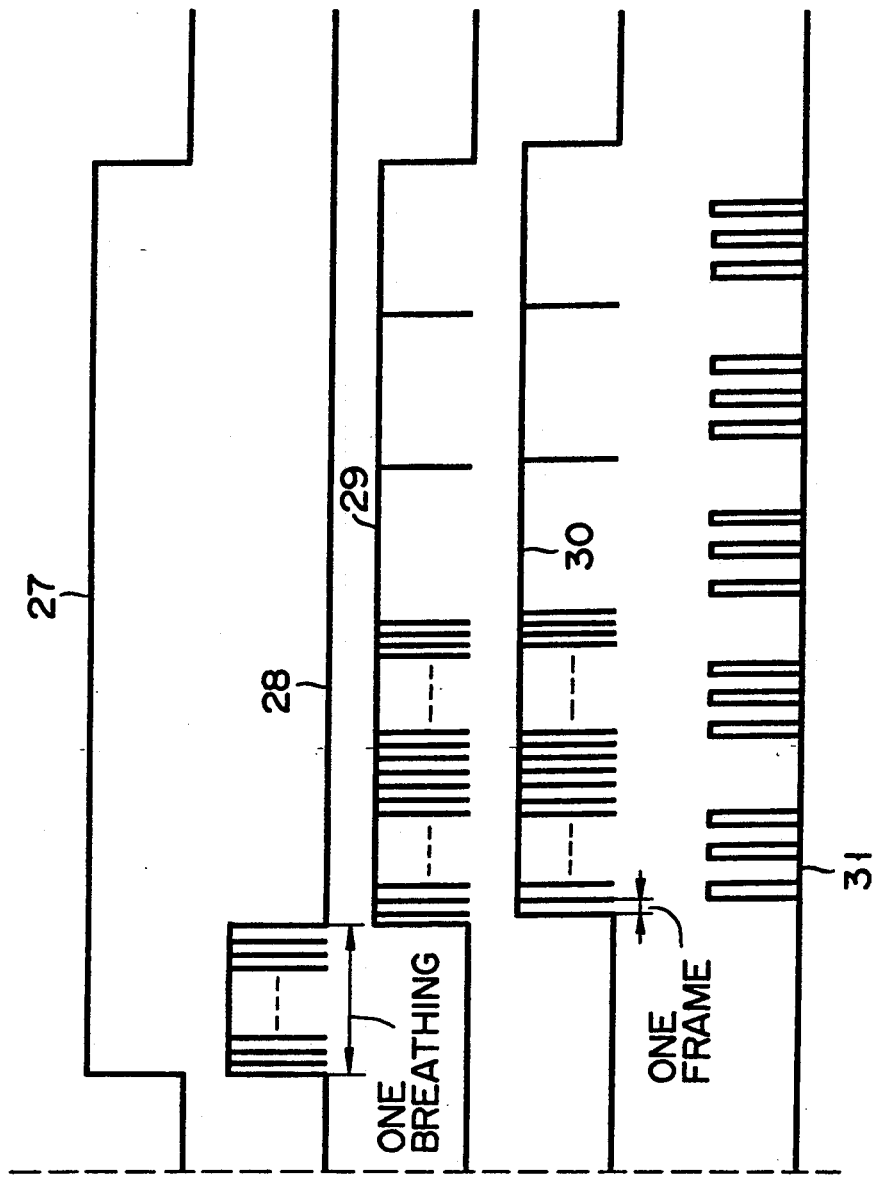

DESTROYING WAVE TREATMENT APPARATUS

BACKGROUND OF THE INVENTION

This application is a continuation of application Ser. No. 340,352, filed Apr. 19, 1989, abandoned.

1. Field of the Invention

The present invention relates to a destroying wave treatment apparatus for destroying or disintegrating an object, such as cancer cells and calculus, that exists in a subject, by irradiating the object with the converged radiation energy of destroying waves.

2. Description of the Related Art

A typical example of the destroying wave treatment apparatus is an ultrasonic treatment apparatus using ultrasonic waves as destroying waves. The ultrasonic treatment apparatus is usually provided with an ultrasonic transducer, or a disintegrating transducer, for forming a focal point of an ultrasonic wave for destroying or disintegrating an object, such as calculus, within a subject, such as a patient, and another ultrasonic transducer, or an imaging ultrasonic transducer, for collecting tomogram data of the human body. In operation, the imaging ultrasonic transducer is driven and a state of an affected part (suffering from a calculus, for example) is displayed on a monitor screen. Then, an operator drives the ultrasonic transducer to emit an ultrasonic wave to the calculus, thereby to destroy it, while looking at the image on the screen. More precisly, a marker indicating a focal point of the destroying ultrasonic wave appears on the screen. The operator moves the marker to set it at the affected part. Then, an operator transmits the destroying ultrasonic wave to the affected part including a calculus, and destroys the calcalus. In this type of the ultrasonic treatment apparatus, a counter is used for counting the number of shots of ultrasonic wave. When a count of the counter reaches a preset number of shots, the operator stops the transmission of the destroying ultrasonic wave, and displays again the tomogram of the human body including the affected part and check if the calculus has been completely disintegrated.

As has been just mentioned, the preset number of shots of the radiated ultrasonic wave is used for judging the timing of the start and stop of transmitting the destroying ultrasonic wave. Accordingly, it is very difficult to check if the calculus has actually be disintegrated during the transmission of the destroying ultrasonic wave. This fact implies that there is the possibility that even after the calculus has been disintegrated, the intensive and dangerous ultrasonic wave may continuously be applied to the affected part of the human body, and that before the disintegration of the calculus is completed, the transmission of the ultrasonic wave may be stopped. The former possibility is the problem to be solved immediately because the continuous radiation of such a destroying ultrasonic wave is harmful to the human body. The latter possibility creates a problem that a long time is consumed for the treatment, because the above sequence of disintegrating operations must be repeated until the calculus will be completely destroyed.

SUMMARY OF THE INVENTION

Accordingly, an object of the present invention is to provide a destroying-wave treatment apparatus which is capable of checking a state of the destruction of an object during the transmission of a destroying wave to the object.

To achieve the above object, there is provided a destroying wave treatment apparatus of the type in which a destroying wave is transmitted to an object to destroy the object within a subject, comprising:

tomogram data collecting means for collecting tomogram data of the object before a destroying wave is transmitted, and tomogram data during the progress of transmitting the destroying wave;

image processing means for forming a subtraction image from the tomogram data before and during the transmission of destroying wave, and for visually presenting a state of the destruction of the object; and display means for displaying a tomogram as obtained by said image processing means.

With such an arrangement, an operator may check a state of an disintegration of the object within an subject while a destroying wave is being transmitted toward the object. Accordingly, the present invention has successfully solved the problem that after the object has completely be destroyed, an unnecessary dangerous destroying wave is continuously applied to the subject. Further, the present invention has succeeded in solving the problem that the transmission of the destroying wave to the subject is stopped before the object is destroyed completely. Consequently, the present invention can secure a safety of the subject, and further reduce a treating time.

BRIEF DESCRIPTION OF THE DRAWINGS

FIGS. 4A to 4C are respectively pixel gradations in the above tomograms and the subtraction image, the illustrations respectively corresponding to those of FIGS. 3A to 3C;

FIGS. 5A and 5B show the states which an object to be destroyed assumes before and during the transmission of a destroying wave toward the object;

FIGS. 6 is a diagram showing images displayed on a monitor screen, the first two images being tomograms obtained before and during the transmission of a destroying wave, and the last image being a subtraction image obtained by subtracting the tomograms;

FIGS. 7A to 7E show timing diagrams for explaining an operation of the diagnosis apparatus of FIG. 1; and FIG. 8 is a diagram showing tomograms on a monitor screen which are displayed by a destroying wave treatment apparatus according to another embodiment of the present invention, one of the tomograms displayed having beam obtained before the transmission of a destroying wave, and the other having been obtained after the transmission of the same.

DETAILED DESCRIPTION OF THE PREFERRED EMBODIMENTS

Preferred embodiments of a destroying wave treatment apparatus according to the present invention will be described with reference to the accompanying drawings.

Figure 1:
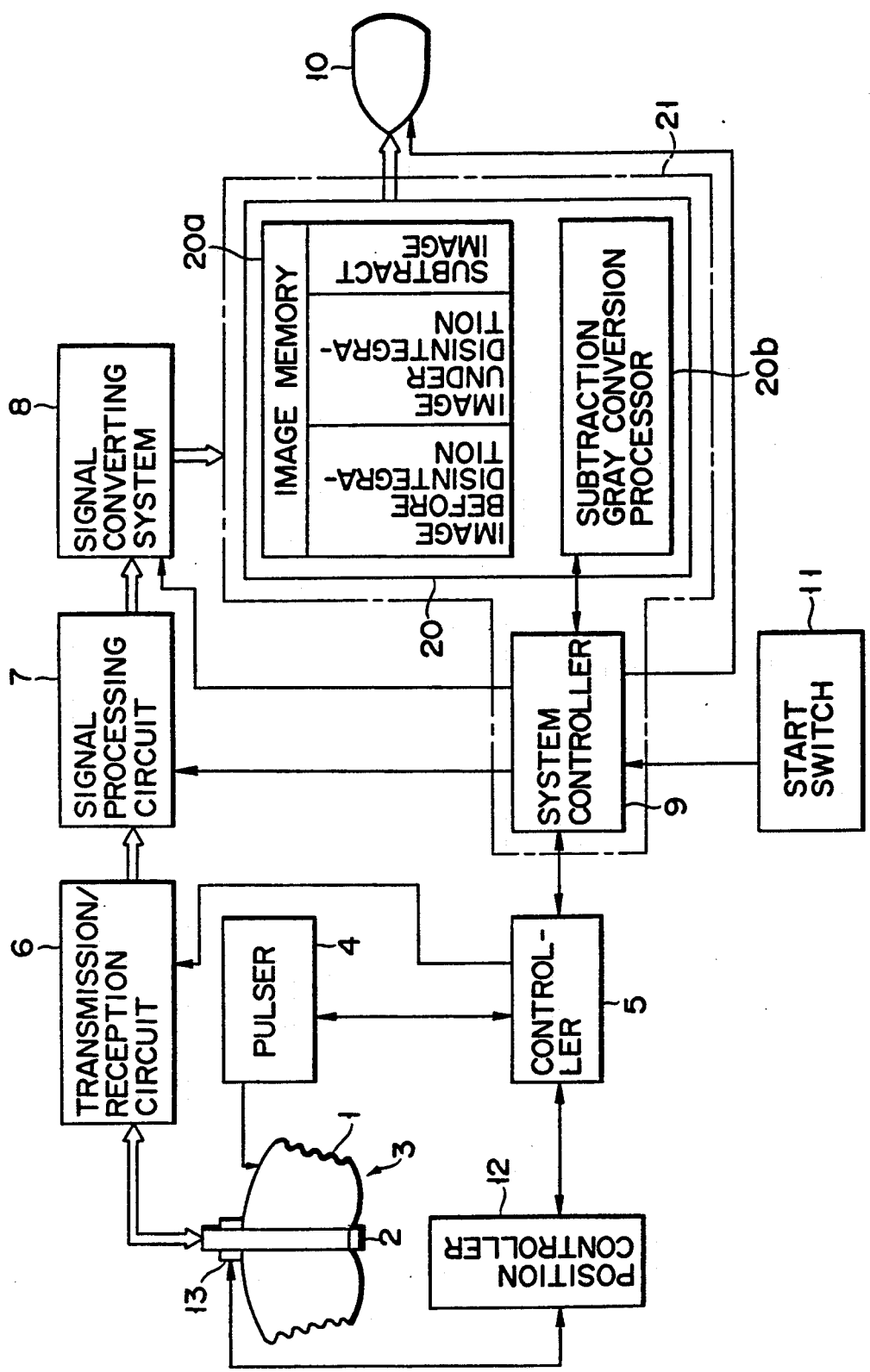
FIG. 1 is a block diagram showing an arrangement of a destroying wave treatment apparatus according to the present invention.

A destroying wave treatment apparatus, which is an embodiment of the present invention, is illustrated in block form in FIG. 1. In the embodiment, an ultrasonic wave is used for the destroying wave. As is shown, the destroying wave treatment apparatus is supplied by a destroying wave applicator 3 which comprises a destroying wave transducer 1 for forming a focal point of a destroying ultrasonic wave that is for destroying an object such as calculus, within a subject such as a patient, and an imaging ultrasonic transducer 2 for transmitting and receiving an ultrasonic wave to form an acoustic domain containing a focal point of the ultrasonic wave as formed by the destroying wave transducer 1. A pulser 4 applies a pulse signal to the destroying wave transducer 1. A transmission/reception circuit 6 transmits a pulse signal to the imaging ultrasonic transducer 2 by a controller 5, and excites the transducer 2 so that it makes a sector scan. The circuit 6 receives an echo signal from the transducer 2 which results from the sector scan. A signal processing circuit 7 receives an output signal of the transmission/reception circuit 6, and amplitude detects the signal, and applies it, as a video signal, to a signal converting system 8. A system controller 9, comprising mainly of a CPU (central processing unit), controls the related sections in the treatment apparatus by using given parameters. A controller 5, under control of the system controller 9, controls the timings of transmitting and receiving the respective pulse signals, and amplitudes and frequencies of the pulse signals in the transmission/reception circuit 6, signal processing circuit 7 and pulser 4. The signal converting system 8, which also under control of the system controller 9, appropriately processes the output signals of the transmission/reception circuit 6 and the signal processing circuit 7. An image processor 20 is made up of an image memory 20a and a subtraction/gray conversion processor 20b. The image memory 20a stores tomogram data outputted from the signal converting system 8. The subtraction/gray conversion processor 20b forms a subtraction image from the tomogram data stored in the image memory 20a in response to a control signal from the system controller 9, and applies a gray converting processing to the subtraction image. A display 10, also controlled by a control signal from the system controller 9, displays tomograms output from the image processor 20, subtraction images (also outputted from the image processor 20) showing states of a calculus before a destroying wave is transmitted and during the progression of transmitting the wave, an acoustic domain in a sector fashion that is formed by the imaging ultrasonic transducer 2, and markers representative of focal points of the destroying ultrasonic wave. A start switch 11 is connected to the system controller 9 in order to set a timing of generating a pulse signal by the pulser 4 for transmission to the destroying wave transducer 1, and is provided with a switch (not shown) to designate the start of transmitting the pulse signal. A position controller 12 is used for adjusting a relative position of the imaging ultrasonic transducer 2 to the destroying wave transducer 1.

In this embodiment, the imaging ultrasonic transducer 2 has two functions; one to collect tomogram data of the calculus before the destroying wave is transmitted to the patient, and the other to collect tomogram data when the destroying wave is being transmitted. To select one of these functions, a function selector switch (not shown) is installed and may manually be operated by an operator.

A display control means 21 comprises the system controller 9 and the image processor 20. The display control means 21 controls the displaying operation of the display 10, when the above two functions are executed, tomogram data of the calculus are collected, a subtraction images is formed from the collected tomogram data, and states of the calculus, destroyed and not destroyed, are to be displayed.

Figure 2:
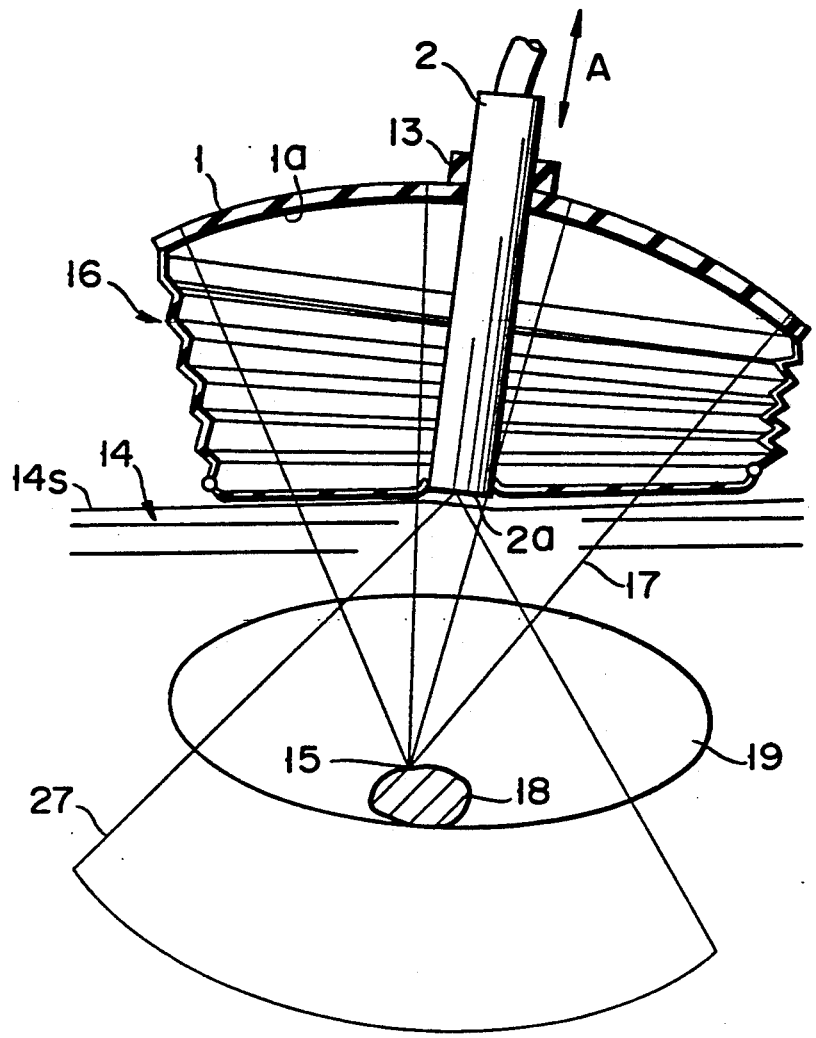
FIG. 2 shows a sectional view of a destroying wave applicator 3 used in the treatment apparatus shown in FIG. 1, the illustration also showing how the applicator is used.

The destroying applicator 3 will be described in details with reference to FIG. 2.

As shown, the applicator 3 is made up of the destroying wave transducer 1, a water bag 16, and the imaging ultrasonic transducer 2. The transducer 1 converges an ultrasonic wave (e.g., an intensive ultrasonic pulse) to destroy or disintegrate a calculus of the kidney 18, for example, of a human body. The water bag 16 is provided on an ultrasonic wave emitting surface 1a of the destroying wave transducer 1. The imaging ultrasonic transducer 2 is disposed in an ultrasonic wave region 17 ranging from the ultrasonic emitting surface 1a to a focal point 15 of the emitted ultrasonic wave. To collect the tomogram data by the imaging ultrasonic transducer 2, an ultrasonic transmission/reception surface 2a of the imaging ultrasonic transducer 2 is placed on the surface 14S of the human body, and an acoustic domain 27 including the focal point 15 is formed. The imaging ultrasonic transducer 2 is movable in the direction of arrow A, in response to a control signal derived from the position controller 12. A signal from a position sensor 13 is used as a reference signal for the movement.

The operation and beneficial effects of the destroying wave treatment apparatus thus arranged will be described. The water bag 16 of the applicator 3 is placed on the surface 14S of the subject 14. Under this condition, the ultrasonic transducer 2 is driven through the transmission/reception circuit 6, signal processing circuit 7, and signal converting system 8. Finally, tomograms of the subject 14 are displayed by the display 10.

In this case, the display 10 displays markers representing the focal points of the destroying waves emitted from the destroying wave transducer 1 at a fixed positions on the monitor screen, by the signals transferred between the system controller 9 and the signal converting system 8. A tomogram of the subject 14 displayed in real time changes its displayed location as the destroying wave applicator 3 is moved. At the stage that the calculus image 18 appears in the tomogram, an operator further adjusts the applicator 3 in fine steps, so that the marker (not shown) is set at the calculus image 18, and under this condition the destroying applicator 3 is fixed.

Figure 3A:
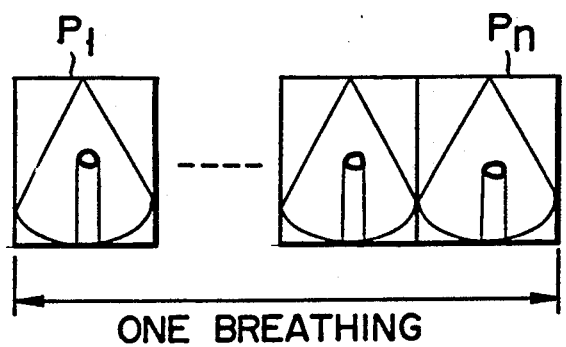
FIGS. 3A to 3C are diagrams showing tomograms obtained within one breathing period before and during the transmission of a destroying wave, and a subtraction image resulting from the tomograms.
Figure 3B:
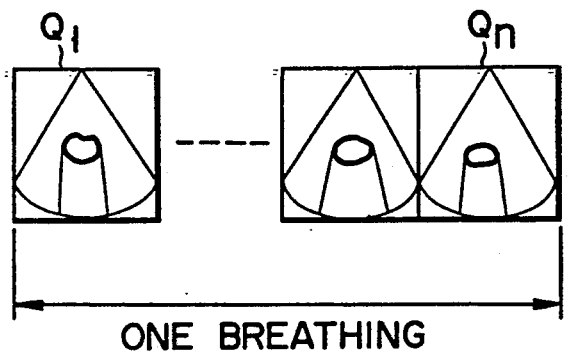
Figure 3C:
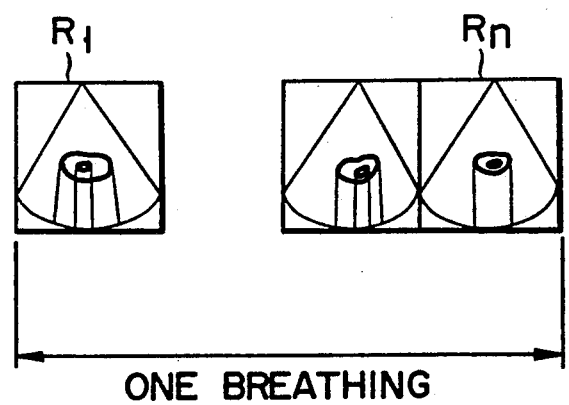

At the time the destroying wave is not yet emitted, the operator pushes the start switch 11 to start a treatment. When the switch 11 is turned on, an operation waveform is timed as shown in FIG. 7A. A tomogram of the calculus collected by the imaging ultrasonic transducer 2 before a destroying wave is transmitted, is stored into the image memory 20a, through the transmission/reception circuit 6, signal processing circuit 7, and signal converting system 8. In addition to the tomogram of the calculus before it is disintegrated, the image memory 20a stores tomograms during the progress of disintegration and a subtraction image formed by those tomograms. A plurality of tomograms are obtained during a period of one breathing of a human body. Tomograms before disintegration of the calculus are denoted as Pl to Pn in FIG. 3A. Tomograms during the progress of disintegration are denoted as Q1 to Qn in FIG. 3B. Images resulting from the subtraction of the two tomograms are denoted as R1 to Rn and shown in FIG. 3C. The plurality of tomograms, each of one frame, are obtained within one breathing period at the timings shown in FIG. 7B. From the next breathing, tomograms of the calculus being currently disintegrated are formed at the timings shown in FIG. 7C in successive order. A subtraction image, that corresponds to a tomogram under disintegration also corresponding to a tomogram after disintegration, appears after one frame from one tomogram under disintegration, as shown in FIG. 7D. Each subtraction image is formed by the subtraction/gray conversion processor 20b, and is subjected to a gray conversion processing in accordance with a gradation of the subtraction image data in gray level.

A pixel gradation in the calculus image 18 before a destroying ultrasonic wave is transmitted (FIG. 3A) is distributed as indicated by a curve 22 in FIG. 4A. A pixel gradation of the same when the ultrasonic wave is being transmitted is distributed as by a curve 22' in FIG. 4B. When these pixel gradations are subtracted, a curve 23 in FIG. 4C is obtained corresponding to the tomogram of FIG. 3C. As is shown, the pixel gradation curve of the subtraction image declines below a zero level, viz., to the negative region, at two locations. To distinctively show a state of a disintegration of the calculus image 18, the curve 23 may be colored in a manner that the parts 23a of the curve 23 existing in the negative region are colored blue and the remaining parts of the curve existing in the positive region are colored red. Profiles shown in FIGS. 5A and 5B are respectively the calculus image 18 before the calculus is disintegrated and that when it is undergoing the disintegration. Those profiles respectively correspond to the pixel gradations of FIGS. 4A and 4B, respectively.

The tomograms before and during the transmission, and the subtraction images are displayed at a speed of 30 frames/second on the monitor screen of the display 10. An operator transmits the destroying ultrasonic wave to the calculus of the human body at predetermined intervals (FIG. 7E), while seeing the subtraction images on the screen.

The display 10 presents a display which contains three images, tomograms 24 and 25 before and during disintegration and a subtraction image 26, as shown in FIG. 6. When an operator treats a patient suffering from a calculus of the kidney, for example, he can exactly grasp a state of the calculus when carefully observing the above three images. Accordingly, when he judges that the disintegration of the calculus is almost completed, he stops the transmission of the ultrasonic wave. When it is not yet completed, he continues the transmission of the ultrasonic wave.

As seen from the foregoing description, a state of a disintegration of a calculus, for example, can be checked by a simple and easy operation, even when the transmission of a destroying ultrasonic wave progresses. Accordingly, there is no danger that after the disintegration is completed, the radiation of the intensive and dangerous ultrasonic wave for a patient, for example, still continues. Further, there is eliminated such a situation that the transmission of the ultrasonic wave is stopped when the disintegration of the calculus is not yet completed, and before the transmission must be repeated until it is completed. Consequently, a safety of the patient and a reduction of treating time can both be attained.

In the above-mentioned embodiment, the destroying wave treatment apparatus is so designed that an operator starts and stops the transmission of the ultrasonic wave while observing the subtraction image. It is evident, however, that some modifications of the embodiment are allowed within the scope of the invention. One of the modifications of a destroying wave treatment apparatus according to the present invention will be described below.

In this modification, a value of a phantom or a negative region (area) of a subtraction image in which an object is destroyed is preselected on the basis of the clinical experiences and stored in the image processor. When a value of the negative region of a subtraction image obtained exceeds the preset value, the transmission of an ultrasonic wave is automatically stopped. This embodiment may attain the above useful effects and lighten an operator's load in his diagnosing work.

It is also evident that the destroying wave treatment apparatus is applicable to disintegrate a gallstone While in the above-mentioned embodiment, the display 10 displays three types of images, tomograms formed before and during disintegration, and a subtraction image, as shown in FIG. 6, the object of the present invention may be attained with a display of only two types of images, viz., the tomograms formed before and after disintegration, as shown in FIG. 8. The display of those tomograms on the same monitor screen will suffice for an exact grasp of a state of a disintegration of the destroyed object by an operator.

It is apparent that a plurality of displays may be used in place of a single display as in the above-mentioned embodiments.

As set out above, the present destroying wave treatment apparatus is characterized in that an object to be destroyed can simultaneously be displayed as tomograms before and during the destruction of the object.

It is further understood that the present invention is not limited to the above-mentioned embodiments, but may variously be changed and modified within the scope and spirits as set forth in the appended claims.

What is claimed is:

1. A destroying wave diagnosis apparatus of the type which comprises a generating means for transit destroying wave to a subject a destructive wave to destroy an object within the subject, said apparatus comprising:
   tomogram data collecting means for collecting tomogram data of the object obtained before a destroying wave is transmitted, and tomogram data obtained during the progress of transmitting the destroying wave; and
   a display means for displaying simultaneously a tomogram of the object obtained before the transmission of the destroying wave and a tomogram obtained during the transmission of the same, on the basis of the tomogram data collected by said collecting means.

2. The apparatus according to claim 1, wherein said display means computer means for displaying a tomogram of the object obtained before the transmission of the ultrasonic destroying wave, a tomogram obtained during the transmission of the same, on the basis of the tomogram data collected by said collecting means, and a subtraction image from the tomogram data before and during the transmission of the destroying wave.

3. The apparatus according to claim 1, further comprising image processing means for forming a subtraction image from the tomogram data before and during the transmission of the destroying wave, and for visually presenting a state of destruction of the object.

4. The apparatus according to claim 3, wherein said image processing means includes a memory means for storing tomogram data of the state of destruction of said object and means for obtaining a subtraction image from the tomogram data stored in the memory means and for subjecting the subtraction image data to a gray conversion processing.

5. An apparatus as in claim 1, wherein said generating means comprises means for transmitting an ultrasonic destroying wave.

* * * * *

UNITED STATES PATENT AND TRADEMARK OFFICE
CERTIFICATE OF CORRECTION

PATENT NO. : 5,005,580
DATED : April 09, 1991
INVENTOR(S) : Kiyoshi Okazaki It is certified that error appears in the above-identified patent and that said Letters Patent is hereby corrected as shown below:

Claim 1, column 6, line 47, after "a" insert
--destroying wave.

Claim 1, column 6, line 47, change "transit"
to --transmitting--.

Claim 1, column 6, line 47, delete [destroying wave].

Claim 1, column 6, line 48, delete [destroying wave].

Claim 2, column 6, line 64, delete [ultrasonic].

Signed and Sealed this

Twenty-sixth Day of October, 1993

*Attest:*

BRUCE LEHMAN

*Attesting Officer*     Commissioner of Patents and Trademarks